(12) United States Patent
Wilson

(10) Patent No.: US 6,524,809 B1
(45) Date of Patent: Feb. 25, 2003

(54) ANALYTICAL METHOD USING MULTIPLE VIRUS LABELLING

(75) Inventor: Stuart Mark Wilson, London (GB)

(73) Assignee: Microsens Biophage Limited (GB)

( * ) Notice: Subject to any disclaimer, the term of this patent is extended or adjusted under 35 U.S.C. 154(b) by 0 days.

(21) Appl. No.: 09/701,857

(22) PCT Filed: Jun. 4, 1999

(86) PCT No.: PCT/GB99/01636

§ 371 (c)(1),
(2), (4) Date: Dec. 1, 2000

(87) PCT Pub. No.: WO99/63348

PCT Pub. Date: Dec. 9, 1999

(30) Foreign Application Priority Data

Jun. 4, 1998 (GB) ............................................. 9811977
Jan. 20, 1999 (GB) ............................................. 9901132

(51) Int. Cl.⁷ .......................... C12Q 1/06; C12Q 1/70; C12N 1/00
(52) U.S. Cl. ............................. 435/39; 435/5; 435/810
(58) Field of Search ................................ 435/5, 39, 810

(56) References Cited

U.S. PATENT DOCUMENTS

| | | | | |
|---|---|---|---|---|
| 4,104,126 A | 8/1978 | Young | ..................... | 195/103.5 |
| 6,165,722 A | 12/2000 | Gershoni et al. | ............... | 435/6 |

FOREIGN PATENT DOCUMENTS

| | | | | |
|---|---|---|---|---|
| EP | 0202688 | 11/1986 | | |
| EP | 0439354 | 7/1991 | ..................... | 1/70 |
| GB | 2060690 | 7/1981 | | |
| GB | WO 9820159 | 5/1998 | ..................... | 1/68 |
| WO | WO 8504189 | 9/1985 | ..................... | 1/70 |
| WO | WO 202633 | 2/1992 | | |
| WO | WO 9317129 | 9/1993 | ..................... | 1/70 |
| WO | WO 9406931 | 3/1994 | | |

*Primary Examiner*—Hankyel T. Park
(74) *Attorney, Agent, or Firm*—Bourque & Associates, PA

(57) ABSTRACT

The present invention relates to a method for detecting a target material in a sample, which method comprises the steps of: a) exposing a sample, expected to contain that target material, to at least two viruses which are capable of binding directly or indirectly with that target material so as to form a virally bound target material and to endow the virally bound target material with a distinctive property; and b) cultivating the product from stage a in the presence of an indicator material to which the viruses carried by the virally bound target material attach so as to cause the indicator material to adopt the distinctive property of the virally bound target material; and c) monitoring the presence or otherwise of virally attached indicator material. The invention also provides a kit for use in the method of the invention.

23 Claims, No Drawings

ANALYTICAL METHOD USING MULTIPLE VIRUS LABELLING

The present invention relates to a method for detecting materials, notably to a method in which two or more viral components are attached to the material which endow the material with a detectable property by which the presence of that material may be detected and it presence in a sample verified.

BACKGROUND TO THE INVENTION

Many techniques exist for analysing samples to detect the presence of a material in that sample. For example, chemical analysis, chromatographic techniques and spectroscopic techniques can be used to identify individual chemical molecules. However, such techniques cannot readily be used to identify organisms present in a sample.

Nucleic acid methods, such as deoxyribonucleic acid (DNA) hybridisation can be used to detect DNA or ribonucleic acid (RNA). However, these methods lack sensitivity. Amplification methods, such as the polymerase chain reaction (PCR), can be used to amplify nucleic acid targets which can then be detected. However, such approaches are complex and expensive and are specific for the detection of nucleic acids.

Immuno methods such as Western blotting or enzyme immunoassay (EIA) or enzyme labelled immuno-absorbent assay (ELISA) can be used to detect a given molecule, for example a protein. However, these methods have detection limits in the picamol (pmol) to sub-picamol per liter range and thus are not suitable where very low levels of the material to be detected are present.

In order to increase the sensitivity of such detection methods, it has been proposed to label the detecting antibody with radioactive materials, enzymes, gold particles or bacteriophage. However, these proposals are often non-specific due to the non-specificity of the attachment of the label to the target or other materials present in the sample being assessed.

It has been proposed in for example PCT Application No WO92/02633 to identify bacteria in a sample by treating the sample in a first cultivation stage with a virus, or phage, which is specific to and infects the bacterium expected to be present in the sample. The infected sample is then treated to kill or remove any exogenous phage particles, that is those which have not infected the bacterium cells and are thus protected within the cell. The resultant bacterial cells are then cultured in a second cultivation stage to cause the phage particles protected within the infected bacterium cells to replicate and lyse. This releases a new generation of phage particles into the culture medium. These can be detected by carrying out the second cultivation stage in the presence of further of the first bacterium cells and detecting the dead bacterium cells formed with each replication of viral particles within an infected cell. Alternatively, the proteins released by the lysis of the viral particles can be detected by protein staining or other methods.

If the expected bacterium is present in the initial sample, viral particles will be present in the infected bacterium cells from the first cultivation of the sample and will be detected in the second cultivation stage. However, if the sample did not contain the expected bacterium, no infection of the sample cells would occur in the first cultivation stage, so that no viral particles would be carried over to replicate and lyse in the second cultivation stage.

This technique is known as the phage amplification technique.

In a modification to the phage amplification technique proposed in PCT Application No WO97/22713, the second cultivation stage is carried out in the presence of a susceptible bacterium which has a replication rate greater than that used in the first cultivation stage. In this way slow growing bacteria, for example Mycobacterium tuberculosis, can be detected rapidly due to the acceleration effect of the second cultivation stage.

However, both variations of the phage amplification technique require that a virus which is specific to and can infect the expected bacterium be used, which severely limits the range of materials which can be identified and the range of viral particles which can be used.

Not only would it be desirable to detect specific organisms in a sample, but it is also desirable to detect a wide range of other materials in samples. For example, it is often desired to detect heavy metals and other contaminants in water or in waste products, to determine whether two or more materials interact with one another in a manner which could affect a user or the environment. Specifically, it would be desirable to provide a simple but effective means for determining the effect of a medicament or pharmaceutical on an organism or medical condition which it is desired to treat with the medicament or pharmaceutical. In vitro homogeneous immunoassay techniques, such as scintillation proximity and fluorescence polarisation/fluorescence quenching are used to report on molecular interactions in screening assays.

These assays are fast and simple to carry out, but generally have a low sensitivity. The yeast two hybrid system is used as an in vivo assay system, where interacting proteins act as a promoter of gene transcription, thereby indicating molecular interactions within the cell. However, this protein/protein interaction can be disrupted by the medicament under assessment. The yeast two hybrid system also requires that the components of the assay be synthesised within the yeast cells. This limits the range of molecular interactions which can be studied.

I have now devised a method which can be applied to the detection of a wide range of materials and the products of the interaction of such materials, so as to provide an assay technique which has widespread application. The method of the invention can use a wide range of marker materials to identify the materials to be detected giving the user flexibility in the materials which are used.

In the method of the invention two different viral particles or active components of a virus are attached directly or indirectly as tags to the material to be detected, hereinafter denoted as the target material. These tags endow the target material with characteristic properties which distinguish the tagged material from the properties of either of the viral particles individually. The tagged material is then examined for the presence or otherwise of these distinctive properties by cultivating the tagged material in the presence of a bacterium which can be infected by the two viruses.

The term virus is used herein to denote true viruses and organisms which infect bacteria in manner similar to a true virus. Thus, the term virus includes:

a. Components of a virus which have the characteristics of the virus from which they are derived;

b. Packaged phagemids, which are crosses between plasmids and viruses and can grow as plasmids in bacterial hosts, but which can be packaged and secreted as if they were viral particles in the presence of a helper virus although they cannot independently produce viral progeny;

c. Viruses which are lysogenic for bacteria and can grow, replicate and produce progeny in the bacteria without lysis of the bacteria which can continue to grow and replicate.

If viral infection of bacterial cells is carried out using an excess of bacteria over that required to achieve parity between the infecting viruses and the infectable bacterial cells, a given bacterium cell is unlikely to be infected by more than one virus particle. The amount at which such dual infection becomes sufficiently unlikely that it will not distort the results of the assay method of the invention can be calculated statistically and is denoted herein as the statistical amount. Such a statistical calculation can be confirmed by simple trial and error tests.

In the method of the invention, two viral particles are physically linked together through the target material and can thus each infect the same bacterial cell so as to endow that cell with both of the characteristic properties of the infecting viruses. A bacterial cell infected by both viruses and possessing the sum of the two characteristic properties can readily be distinguished from cells which possess only one of those properties. For example, the infected cells can be cultivated under conditions under which the cells possessing only one of the properties cannot survive, for example in the presence of specific antibiotics or specific temperature or pH conditions. The infected cells having both characteristic properties survive and will replicate. If lysogenic viruses are used as the tags to be attached to the target material, the viruses will replicate within the infected bacterial cells and produce progeny virus particles which will be released to begin further cycles of infection and replication. Thus, in the presence of tagged target material a cascade of bacterial growth indicates that the target material was present in the initial sample. If no tagged material is present in this cultivation stage, little or no bacterial growth will take place.

SUMMARY OF THE INVENTION

Accordingly, the present invention provides a method for detecting a target material in a sample, which method comprises the steps of:

a. Exposing a sample, expected to contain that target material, to two or more viruses which are capable of binding directly or indirectly with that target material so as to form a virally bound target material and to endow the virally bound target material with a distinctive property; and b. Cultivating the product from stage a in the presence of an indicator material, preferably in excess over the statistical amount, to which the viruses carried by the virally bound target material attach so as to cause the indicator material to adopt the distinctive property of the virally bound target material; and c. Monitoring the presence or otherwise of virally attached indicator material.

The invention can be applied to samples in which the target material is present or in which it is to be generated by the interaction of other components within the sample or by the interaction of a component of the sample with an external component added thereto. For convenience, the term sample containing a target material will therefore be used generally to denote a material in which the target material is present ab initio or in which the target material is generated by some mechanism.

The method of the invention can be used to assess the presence and the approximate amount or concentration of the target material in the sample and may be carried out to give a quantitative assessment of the target material as well as to detect simply the presence or otherwise of the target material. In some instances, it may be possible to monitor the generation of target material in a sample by monitoring the development of some secondary feature, for example colour, in the product from stage b. For convenience, the term detect will be used herein to denote both qualitative and quantitative assessment of the target material in a sample and the detection may be carried out intermittently or continuously over a period of time or as a single observation.

Preferably, the cultivation stage b is carried out under conditions under which the virally attached indicator material survives but under which indicator material to which none or only one of the viruses have attached does not survive.

As indicated above, it is necessary for at least two different viruses to become attached to the target material so that cultivation conditions for stage b can be selected to ensure that only the indicator material having the properties endowed by both viruses survives. Typically, the viruses used are different species, each imparting a different property to the virally bound target material and hence to the indicator material. However, it is within the scope of the present application to use the same species of virus and to modify the virus using known techniques to introduce desirable components not normally present in the virus so as to impart the desired properties to the viruses used in the method of the invention. For example, a virus can be treated in known manner to introduce a genotype which imparts resistance to certain antibiotics. This may be done for each of the viruses which are to be bound to the target material. Such modification can be to introduce other properties into the virus, for example heat or light sensitivity, so that the conditions under which the cultivation in stage b are carried out can engender or reflect a wide range of properties in the indicator material.

As indicated above, the virus is bound to the target material so as to endow the target material with at least two different properties. If desired, the target material may be endowed with additional properties carried by the viruses or additional viruses which enable or facilitate detection of the virally attached indicator material. For example a third virus can be bound to the target material which endows the virally bound target material with photo-luminescent properties. The presence of the virally bound target material can thus be readily detected by illuminating the product from stage b with UV, IR or visible light to cause the material carrying the third virus to illuminate. Alternatively, the property could be the expression of an enzyme not normally expressed by the indicator material, for example B-galactosidase, luciferase, or alkaline phosphatase.

For convenience, the invention will be described hereinafter in terms of binding a virus which has been modified to carry one genotype which endows resistance to anti-biotic A and another virus which has been modified to carry another genotype which endows resistance to anti-biotic B.

The target materials may be part of a virus, bacteria, protozoa, eukaryotic cells, fungi or other organisms or parts of organisms. However, the target material may be a residue from an organism, for example a protein secreted or generated by the organism, a hormone, a nucleic acid or sequence of acids, a prion or an antibody. Alternatively, as indicated above, the target material may be a chemical, for example a medicament or biocide, for example a pesticide, hebicide or fungicide, whose efficacy is to be assessed against specific organisms, or a chemical which is produced by the interaction of two other materials, for example a hormone or protein, and whose presence in the sample gives a measure of the efficacy of a material under assessment in preventing or aiding generation of that hormone or protein; or an impurity or pollutant organic or inorganic chemical whose presence, for example in water or a product, could give rise to health or other hazards. Due to the variety of components which can be tagged with the viruses, the invention can be applied across a wide range of applications where it is necessary to detect very low levels of a material, typically less than about 100 parts per million.

The target material ideally presents two sites at which a virus can bind directly to the target material. Such binding of the target material can be directly to the virus, for example through suitable sites on the surface of the virus particle or through a site which has been modified in known manner to bind to the target material. However, it is within the scope of the present invention to bind either or both of the viral particles to the target material through an intermediate binding material or ligand, for example a protein, amino acid, lectin, peptide, antibody, monoclonal antibody, nucleic acid or other material which recognises different regions of the target material. Alternatively, the genetic sequence encoding the ligands can be inserted into the virus genome and expressed on the surface of the viral particle. If desired, the site to which a viral particle is to bind can have been flagged with different haptens, for example biotin and dinitrophenol (DNP), and the different viral particle cross-linked with anti-biotin and anti-DNP antibodies so that the viral particles are guided to the binding sites on the target itself or the ligand.

The term binding of the virus to the target material is therefore used herein to denote attachment of the virus by any means to the target material, whether directly or indirectly, so as to provide sites which retain the activity of the virus operatively associated with the target material.

Suitable pairings of the target material, virus and ligands can readily be established using known techniques and the selections verified by simple trial and error tests. Since the possible combinations of virus and ligand enable a wide range of materials to be formed which can bind to a given target material, and since a wide range of modifications can be achieved to different species of virus, the invention can be used to form a virally bound target with a wide range of target materials, which are not limited solely to bacteria, as with the viral amplification assay techniques proposed hitherto. The invention thus finds widespread use wherever it is desired to detect the presence of a material in a wide range of samples.

The binding of the virus or modified virus to the target material may be carried out using a wide range of methods and materials, depending upon the nature of the target material. Typically, the binding will be carried out by incubating a sample containing the desired target material in the presence of the appropriate viruses, either in a single stage using a mixture of viruses or as two stages where the sites at which the virus particles bind will only accept one type of virus. The incubation is typically carried out at a temperature of from 0 to 60° C. in a suitable liquid medium, notably an aqueous medium. The target material and unbound virus may be in solution, suspension in a liquid phase or may be in solid form or carried upon a solid carrier, for example a nitrocellulose or nylon membrane, a ceramic frit, solid beads or the like. For convenience, the invention will be described hereinafter in terms of the use of an aqueous carrier for the target material. Such a form of the target may be made by dissolving or suspending a freeze dried or other solid form of the virus and target material using known techniques.

The use of two separate components, each carrying its individual virus type, which interact to form a third material carrying both types of virus is a particularly preferred embodiment since this enables rapid screening of drugs which have and affect on the interaction.

The incubation in stage $\underline{a}$ is carried out until a satisfactory proportion of the viral particles have become bound to the target material. The optimum conditions for the viral binding stage will depend upon the nature of the target material, the virus particles and the method used to detect the virally attached indicator material in stage $\underline{b}$. Typically, the viral binding will take from 5 to 180 minutes at a temperature of from near ambient to 60° C., and the optimum period and conditions can readily be determined by simple trial and error tests for any given case. The optimum extent of viral binding to the target material will depend upon the nature of the properties to be detected in the product from stage b and the expected level of virally bound target material in the sample, but will typically achieve viral binding of at least 25%, preferably from 30 to 60% or more, of the target material.

If desired, the virally bound target material formed in stage $\underline{a}$ can be isolated from the mixture in which it was formed using conventional isolation and washing techniques. However, this often will not be necessary and the product from stage $\underline{a}$ may be used directly as the medium in which stage $\underline{b}$ is carried out. However, some partial separation of the virally bound target material from residual free virus particles may be carried out using, for example, filtration or capture with paramagnetic beads. The washing may be carried out with materials which kill or incapacitate free viral particles. Alternatively, where the binding of the viral particles to the target material involves labelling the target material with a tag such as biotin, the virally bound target material may be isolated from the unbound viral particles using such a tag, for example by means of streptavidin paramagnetic beads. I have found that such partial separation or isolation of the virally bound target material from residual unbound phage enhances the sensitivity and specificity of the method of the invention in detecting or localising the target material.

In stage $\underline{b}$, the virally bound target material is cultivated in the presence of an indicator material to which the viral moieties carried by the target material attach. By virtue of their being carried by a single target molecule or particle, the viral moieties will co-attach to the same molecule or particle of the indicator material and endow that molecule or particle with both two distinctive properties with which the target material is endowed. It is therefore possible to differentiate molecules or particles having both properties from molecules or particles having only one property.

The viral moieties may attach to the indicator material in a number of ways. For example, the viral moieties may infect bacterial indicator materials; or may express a genotype during the cultivation which attaches to the indicator material to impart the distinctive properties thereto. However, the transfer of the characteristic properties from the virally bound target material to the indicator material need not require the entry of the viral particles into the cell of the indicator material. Thus, the virus particles may transfer their properties by becoming attached to the exterior of the indicator material.

For convenience, the invention will be described hereinafter in terms of the case where the viral moieties carried by the target material infect the bacterial cells in stage $\underline{b}$ and are protected within the infected cells to impart the distinctive properties to the infected cell.

Thus, stage $\underline{b}$ may be carried out by adding an appropriate bacterial culture to the product of stage a and carrying out the cultivation and infection of the bacteria under conditions in which only those bacteria having both distinctive properties imparted to them survive or are able to replicate. Thus, in the preferred embodiment, cultivation of bacteria such as *E. coli* is carried out in the presence of the two anti-bacterial agents to which the viral moieties carried by the virally bound target material impart resistance. Alternatively, the cultivation in stage b is carried out in the absence of the anti-biotics and the antibiotics are added after the cultivation has been carried out to provide a readily detectable bacteria population. For convenience, the invention will be described hereinafter in terms of carrying out the cultivation of the bacteria in the presence of the anti-biotics so that their effect on the growth of the bacterial cells can be detected in real time.

The *E. coli* is preferably present in a greater amount than would be required to achieve numerical parity between the virally bound target molecules or particles and the bacterial cells, preferably in excess of the statistically required amount. The use of an excess of the *E. coli* reduces the chance that an individual bacterium cell will be infected by individual particles of both viruses which may remain in the product from stage a. However, where the conditions in stage b or subsequently are strongly adverse to the survival or growth of cells infected by only one of the types of virus, it may not be necessary to use an excess of the *E. coli*. Typically, an excess of from 10 to 300% or more of the *E. coli* over the statistical amount will be used to minimise the production of bacteria cells infected with only one type of virus and thus aid detection of the cells infected by the virally bound target material. Furthermore, as stated above, it is preferred to remove unbound virus particles from the product of stage a, which further reduces the risk of production of bacteria cells infected with only one type of virus.

Depending upon the efficacy of the anti-biotic agent used in stage b, the bacterial cells infected by only one virus may die or may not grow and replicate. If lysogenic viruses are used, the dually infected cells can host viral replication. The replicated viral particles from such cells can therefore infect further cells and replicate so that a cascade of infection, replication and release of viral particles can be caused. This has the effect of amplifying the effect of the growth of the dually infected cells.

The growth of the dually infected cells can be monitored using any suitable technique. For example, cultivation of the bacteria can be continued until significant populations of the dually infected cells are apparent to the naked eye. Alternatively, where one of the properties imparted to the target material permits it or where a third virus has been bound to the target material, the growth of the dually infected cells can be monitored by colourimetric, fluorescent or luminescent means. If desired, the cultivation means can incorporate an enzyme or other means which responds to a chemical released from the growing bacterial to enhance the property endowed by one of the viruses carried by the dually infected cells.

The distinctive property imparted to the dually infected bacterial cells varies in intensity according to the number of such cells present in the cultivation mixture in stage b. This intensity can be used to give an indication of the amount of the target material in the original sample as well as showing that the target material was present in the initial sample tested.

If desired, the effect of background coupling of individual phage particles to the target material and their detection in stage b can be reduced using a surfactant, notably a non-ionic surfactant such as that sold under the trade mark Tween or by the use of a protein blocking agent such as casein or albumen in amounts of from 0.1 to 0.5% v/v and up to 5% w/v respectively in the cultivation medium or washing fluids in stages a and/or b.

As stated above, the method of the invention can be applied to a wide range of target materials due to the large number of combinations of materials which can be used. The invention thus finds widespread application in testing samples from a wide range of sources and for a wide range of target materials. The target materials need not be organisms as required in the phage amplification technique, but could be chemicals, for examples proteins derived from the lysis of a virus; RNA produced by living organisms rather than components of the organism itself; heavy metals or other pollutants in water systems; or proteins or nucleic acids in solution or bound to solid support materials, for example polyamide membranes.

The invention also finds use in determining biological activity of materials by determining the effect of that material on suppressing or promoting growth of bacteria or other organisms. Thus, for example, an organism can be exposed to a drug under test and the production of secreted protein or messenger RNA monitored. If the drug is effective, the production of protein or messenger RNA will cease at the point that the drug becomes effective and this can be monitored using any suitable technique. Alternatively, the drug may suppress growth of an organism, for example a fungus or yeast, and the subsequent growth of that organism after treatment with the drug assessed in stage b.

The method of the invention can also be used to investigate whether two or more materials interact to combine or react with one another. In this application of the invention, the materials to be investigated can each act as a target material for one of the phage types and the production of a product which carries both types of phage used to demonstrate that interaction or bonding of the two target materials has taken place. Thus, molecules of one material can be tagged with phage endowing property A and the molecules of the other material tagged with phage endowing property B. If the materials are exposed to one another under the conditions under which the interaction is to take place, and the resultant mixture incubated as in stage b, the presence of molecules or product endowed with both properties A and B can be detected as described above. This technique can be applied to detecting the interaction of two simple and/or complex molecules, for example the bonding of an enzyme onto a substrate, the interaction of two proteins or a protein and a nucleic acid, for example in the screening of drugs. If desired, a third molecule can be endowed with a third property using a different phage to give a complex endowed with all three properties A, B and C. Alternatively, the invention can be used to verify that no interaction takes place, for example where a drug or other material inhibits the interaction by preferentially binding with one of the interacting molecules, and thus indicates whether it is safe to mix certain combinations of materials or whether a drug has an effect on an expected interaction.

In these cases, the invention is used to detect the presence or absence of a combined target material formed by the interaction of two individually virally tagged components which combine to form the target material of the invention carrying the two viral tags. The term target material as used herein is therefore to be construed as including a single material which has been tagged with both types of virus and materials which have been tagged with one of the types of virus and which combine or interact with one another to form the material carrying both types of virus.

Since, in the preferred embodiment, the detection of the target material involves cultivation of dually infected cells, it is possible to continue this cultivation (stage b) until the initial amount of such cells has increased by a large factor, for example 10 to $10^8$ fold. In this way a very small level of the target material in the initial sample can be amplified to a very large extent making it possible to detect levels of target material which might not otherwise be detectable by conventional techniques.

The invention also provides an assay kit for use in the method of the method, which kit comprises:
a. two phage materials which are adapted to bind to a common target material or to individual components which combine to form the target material, which phage materials endow that target material with a distinctive property; and
b. an indicator material suitable for cultivation in a growth medium and adapted to adopt the distinctive property endowed by the phage materials.

Preferably, the indicator material is a bacterium which can be infected by the phage materials. It is further preferred that the kit also comprises a growth medium for the cultivation of the virally bound target material and the indicator material. It is further preferred that the kit comprises an additional ingredient which provides visually detectable indication of the growth of indicator material infected by the phage materials.

DESCRIPTION OF THE PREFERRED EMBODIMENTS

General Description

The invention will now be described by way of illustration in terms of preferred embodiments thereof and in terms of the detection of a target molecule using two different viruses, virus A and virus B. The target molecule may be a protein, which may be in solution or bound to a solid support. Viruses A and B are single-stranded bacteriophage M13 viruses or phagemids which have been modified by insertion of the genes encoding ampicillin and kanamycin resistance respectively. If desired, the viruses can be modified by insertion of the gene encoding the IgG binding domain of the protein. This enables the viruses to be bound to any IgG antibody which can be specific for the target material. Where the target molecule is in solution, either or both viruses A and B can be further modified to include a maltose binding peptide or auto-biotinylation peptide or covalently linked to a hapten such as biotin. This enables the virally bound target material to be washed by capture with streptavidin or maltose-derivatised paramagnetic beads in order to remove any unbound virus. This increases the sensitivity and specificity of the method of the present invention.

Virus A and/or B can also be modified to contain a gene which encodes a detectable marker, such as an enzyme for example β-galactosidase or luciferase, which enables calorimetric, fluorescent or luminescent detection of the virally attached indicator material. If desired virus A and virus B may each contain different components of the detectable marker which are compilated and become functional upon dual infection of the indicator material. A specific example of this is the expression of β-galactosidase following LacZ complimentation of TG1 cells. The expression of the β-galactosidase only occurs upon infection of the TG1 cells with a virally bound target material carrying both the complimentary components of the lac operon. The β-galactosidase can be detected using the inducer isopropyl-β-thiogalactopyranoside and the indicator bromo-4-chloro-3-indolyl-β-galactoside in an agar medium. The medium may contain 4-methylumbelliferyl-β-D-galactose which is fluorescent or luminescent in the presence of β-galacotsidase. It is also within the scope of the invention to monitor the changes in colour or colour intensity intermittently or continuously using a spectrometer, ELISA reader, luminometer or fluorimeter to provide a qualitative estimate of the target material present in the initial sample.

In a variation of this technique, two components which interact to form a third component can each be individually bound to a different phage so that the third component will carry both phage types and can then be detected using the method of the invention. This variation finds especial use in rapid screening of drugs where the action of the drug to inhibit or potentiate the production of the third component can be used to provide a rapid assessment as to whether the drug is likely to have a useful effect in conditions where the first two components, for example proteins, are present or are generated.

In the method of the invention, the virus particles are incubated for 10–120 minutes at a temperature between 4° C. and 50° C. with the sample in which the target molecule is to be detected. During this incubation the viruses become bound to the target protein molecules in the sample. After this incubation, the sample may be either used as such in the cultivation stage b, or isolated, for example using bead capture and washed. Where the sample is bound to a solid support, it can be rinsed with an appropriate wash buffer.

In the cultivation stage b, an excess of *Escherichia coli* (*E. coli*) over the statistically required amount is then added in an appropriate growth media and incubated at a temperature between 4° C. and 50° C. for 30–720 minutes. The growth medium contains both ampicillin and kanamycin so that bacteria which have been infected by only one of the viruses die or do not replicate, whereas those which have been infected by both viruses A and B are resistant to these antibiotics and replicate. This enables an observer to monitor the growth of the bacterial cells in the culture medium and to determine both the presence of growing cells and the number of such cells in real time. However, it is also possible to add the anti-biotics to the culture medium after a suitable incubation period and to determine the effect of the anti-biotic on the cell population. If the anti-biotic is added after the initial incubation stage, a further incubation of between 2–60 minutes would be required in order to generate a detectable change in the incubated material.

In another preferred embodiment for the detection of a molecule such as a nucleic acid, which may be in solution or bound to a solid support, virus A and virus B are single-stranded bacteriophage M13 viruses or phagemids which have been modified by insertion of the genes encoding ampicillin and kanamycin resistance respectively. The viruses may be subjected to further modification by linking to nucleic acid or peptide nucleic acid probes as described below. The viruses are incubated for 30–240 minutes at a temperature between 4° C. and 60° C. with the sample in which the target molecule is to be detected. During this incubation, the viruses bind to the target nucleic acid molecules in the sample.

After this incubation, the virally bound nucleic acid is incubated with an excess of *E. coli* in a suitable growth medium at a temperature between 4° C. and 50° C. for 30–480 minutes and the effect of the anti-biotics assessed as described above.

In the detection of nucleic acids, two or more nucleic acids probes are required which can bind to the target nucleic acid. Single copy gene sequences can be detected by using two probes to the same genetic region or gene, but sensitivity for diagnostic applications may be increased by targeting repeated or repetitive sequences in the genome of the organism to be detected. Such repetitive sequences may be detected by the binding of more than one copy of a single species of probe to the repetitive sequence. If two probes are used they can be labelled with the same or differing haptens eg. both probes can be labelled with biotin or one probe labelled with biotin and the other with digoxigenin (Boehringer Mannheim. Lewes, UK, 1 093 088). After binding (hybridising) the probes to the target nucleic acid, the probe molecules which are now spatially linked can be detected through the hapten groups carried by them. For example, Phage A and Phage K can be used which have been conjugated to fragments of anti-digoxigenin antibody (Boehringer Mannheim, Lewes, UK, 1 214 667) or streptavidin. If a single hapten, eg. biotin, is used to label the probes, then the two phage can be labelled with the same hapten-binding molecule, eg streptavidin. This approach may be adequate for detection of repetitive tandemly repeated molecules, eg. Lmet2 sequence of *Leishmania donovani,* or the 21 base pair repeat of *Plasmodium falciparum.* The target DNA can be prepared from the organism using a suitable conventional technique or in crude extracts or lysates of patient samples and immobilised onto a membrane eg. Hybond N, Hybond N+ (Amersham International plc, Amersham UK) and denatured using standardised methods (Amersham International plc publications P1/384/91/6 and P1/387/92/4 and Short Protocols in Molecular Biology, second edition. Ausubel, FM et al eds. Green Publishing Associates and John Wiley & Sons. 1992) prior to detection. Alternatively, a homogenous assay format can be used; or purified DNA can be prepared, cut by restriction enzymes, size separated by electrophoresis and immobilised onto nylon membranes before detection.

Test Results

Preparation of Log Phase TG1 *E coli*

Minimal media plates were prepared as described in ※ Short Protocols in Molecular Biology※ $2^{nd}$ Edition, edited by F M Ausubel et al, Green Publishing Associates and John Wiley & Sons, 1992. *E Coli* TG1 (Pharmacia Biotechnology, Cambridge, UK※ Expression Module 27-9401-01) was streaked on to the minimal media plate and incubated overnight at 37° C. to generate single colonies and then stored at 4° C. A single colony was inoculated into 10 ml of 2×YT medium containing 17 g Bactotryptone (Difco 0123-17-3), log Bacto yeast extract (Difco 0127-17-19) and 5 g NaCl per liter which had been autoclaved for 15 minutes. The inoculated medium was incubated with shaking at 37° C. until log growth was achieved, OD660 nm of about 0.5.

Preparation of Phage K

10 µl of the log phase TG1 prepared as described above was added to 1 ml of 2×YT in a 20 ml plastic universal container. $10^8$ Phage M13K02 (Pharmacia, Expression module 27-1524-01) pfus were added to the container and the mixture incubated at 37° C. for 60 minutes. 10 mls of 2×YT, 50 µg/ml of kanamycin was added and the mixture incubated at 37° C. until a stationary phase growth was achieved ※ about 5 hours. Cells and cells debris were removed by centrifugation and the supernatant filtered through a 0.22 micron filter. 2 mls of 20% w/v solution of PEG 8000 (Sigma P5413) and 2.5 M NaCl was added to the phage suspension and the phage allowed to precipitate out overnight. The phage was then repeatedly centrifuged and re-suspended then incubated in 1 ml of PBS (Sigma 1000-3), 1 mM of $MgCl_2$ (Sigma M2670) and 25 µM Trypsin (as 6 µl of 2.5% w.v Trypsin stock ※ Sigma T4674) for 60 mins and the phage precipitated with 200 µl of 20% PEG8000 and 2.5M NaCl for 10 minutes at room temperature. The phage was centrifuged and washed with PBS, $MgCl_2$, PEG 800 and NaCl. Fluids were removed and the phage re-suspended to give the active phage carrying the kanamycin genome.

Preparation of Phage A

This phage was prepared using the technique described above for phage K except that phage A pCANTAB 5E from Pharmacia Biotechnology, Expression module 27-9401-01 was used and this was incubated with ampicillin (Sigma A2804) and helper phage M13K07 from Pharmacia Biotechnology, Expression module 27-1524-01 and then with both ampicillin and kanamycin (Sigma K0879) to give a phagemid encoding ampicillin resistance.

Alternatively, phage A and phage K can be prepared and purified by ultracentrifugation on caesium chloride gradients using the technique described in Short Protocols in Molecular Biology.

EXAMPLE 1

Detection of an Immobilised Ligand-binding Molecule Using Phage Labelled with Ligand In this example the ligand used is biotin which binds to the protein streptavidin. One molecule of streptavidin can bind four molecules of biotin.

The biotinylation of the phage was performed using biotinamidocaproate-N-hydroxysulfosuccinimide ester (Sigma B2643) as described in the supplier's handbook. The optimum ratio of phage to biotin can be determined experimentally for each phage. The biotinylated phage were purified by standard polyethylene glycol precipitation.

The biotinylated Phage K and Phage A were used to detect streptavidin paramagnetic beads. The beads had been previously quantitated by light microscopy at $2×10^5$ particles per µl using a haemocytometer. The streptavidin paramagnetic beads (Promega Z5481) were washed and prepared as recommended by the suppliers. Control beads were blocked by washing in the same solution containing 0.1 mM biotin (Sigma B4501).

The streptavidin and blocked control beads were diluted serially ten-fold and incubated with a mixture of each of the biotinylated phage. After allowing the phage to bind to the beads, the beads were washed and incubated with log-phase TG1 cells to achieve phage infection.

After phage infection, the TG1 cells were plated out on solid media containing ampicillin and kanamycin so as selectively to cultivate those *E. coli* cells which had been dually infected cells by both phage A and phage K and the numbers of colonies were counted (see Table 1). The test and blocked control were performed in duplicate (A and B) and the results are set out in Table 1:

TABLE 1

| | Number of streptavidin beads | | | | |
|---|---|---|---|---|---|
| | $2 \times 10^5$ | $2 \times 10^4$ | 2000 | 200 | 20 |
| Test A | ++ | ++ | 576 | 69 | 19 |
| Test B | ++ | ++ | 397 | 97 | 17 |
| Control A | 65 | 2 | 2 | — | — |
| B | 93 | — | — | 3 | — |

++, too many to count

Conclusions

Two phage which encode different selectable properties within their *E. coli* host can be used in an assay to detect a molecule to which they bind by virtue of ligands on the phage surface. The results demonstrate that this test method has a sensitivity of as low as 20 streptavidin beads.

EXAMPLE 2

Detection of a Ligand-binding Molecule (Streptavidin) in a Homogenous Assay (Without Washing)

Serial dilutions of streptavidin (Sigma S4762) were added to a mixture of biotinylated Phage A and Phage K prepared as in Example 1. After incubation to allow the phage to bind to the streptavidin, log-phase TG1 cells were added to infect the *E. coli* cells with the phage.

After infection, the cells were plated out on solid media containing ampicillin and kanamycin to select for dually infected cells and the numbers of colonies on each plate were counted and the results are set out in Table 2:

TABLE 2

| No. moles of streptavidin In reaction | No. molecules streptavidin in reaction | No. colonies |
|---|---|---|
| 1 femtomole | $10^9$ | 43 |
| 100 attomole | $10^8$ | 370 |
| 10 attomole | $10^7$ | 1165 |
| 1 attomole | $10^6$ | 948 |
| 0.1 attomole | $10^5$ | 34 |
| 0 | 0 | 13 |

Conclusion

These results demonstrate that the method of the invention could detect as few as $10^5$ molecules or 0.1 attomoles streptavidin without capture or washing of the complex. Inhibition of detection was apparent at higher concentrations (1 femtomole) of streptavidin, which is a common observation with other immunoassay techniques.

EXAMPLE 3

Detection of an Antigen with Antibody-labelled Phage

Phage A and Phage K were each conjugated to an anti-potato virus X antibody (Agdia Incorporated, Elkhart, Ind. 46514, USA) using glutaraldehyde as the bioconjugate by the method described in Bioconjugation, Mohammed Aslam and Alastair Dent, Eds. 1998. Macmillan Reference Ltd. London, UK ISBN 0-333-583752. The conjugates were diluted and stored in TBS, 1 mM $MgCl_2$ at 4° C.

ELISA kits for detection of Potato Virus X (Agdia, PathoScreen Kit PSP 10000/0288), positive control vials of freeze-dried infected leaf material (Agdia, LPC 10000) and negative control vials of freeze-dried leaf material (Agdia, LNC 10000) were obtained from Agdia Incorporated.

Dilutions of infected leaf material were added to anti-potato X virus antibody coated microtiter plate wells (Agdia, PathoScreen Kit PSP 10000/0288) to allow capture of the viral material. After capture and washing, conjugated Phage A and Phage K were added to each well and incubated to allow capture of the phage particles. The wells were then washed and log-phase TG1 cells were added to enable infection of the cells with the conjugated phage. After infection, the contents of each well were plated out on solid media containing ampicillin and kanamycin to select for dually infected cells and the numbers of colonies on each plate were counted. The results are set out in Table 3:

TABLE 3

| | Number of colonies | |
|---|---|---|
| Dilution of positive control leaf extract | Duplicate test 1 | Duplicate test 2 |
| $10^{-1}$ | ++ | ++ |
| $10^{-2}$ | 388 | 272 |
| $10^{-3}$ | 142 | 114 |
| $10^{-4}$ | 60 | 56 |
| $10^{-5}$ | 104 | 58 |
| $10^{-6}$ | 84 | 35 |
| Negative control | 86 | 40 |

++ too many colonies to count ie. >1000

Conclusion

The method of the invention detected the presence of leaf virus at a $10^{-3}$ dilution of the positive control leaf material.

Comparative Example

Comparison of a One Phage, a Two Phage and ELISA Approach for Detection of Virus The same protocol as described in Example 3 was followed except that use of a single conjugated phage (Phage K) was compared to a mix of conjugated Phage A and Phage K for detection of the diluted plant extracts. The single Phage K was finally plated out on kanamycin-containing agar plates, whereas the phage mix was finally plated out on kanamycin and ampicillin-containing agar plates in the usual way. After incubation to allow selection of infected cells, the numbers of colonies were counted and the results are set out in Table 4:

Following the manufacturers' instructions, a Pathoscreen Potato Virus X ELISA assay was performed in parallel on the same dilutions of positive control leaf extract and the results of this test are also set out in Table 4:

TABLE 4

| Dilution of positive control leaf extract | Phage A and Phage K mix used | Phage K only used | Potato Virus x ELISA (OD450) |
|---|---|---|---|
| $10^{-1}$ | ++ | ++ | 2.30 |
| $10^{-2}$ | 61 | ++ | 0.65 |
| $10^{-3}$ | 11 | 362 | 0.00 |
| $10^{-4}$ | 0 | 89 | 0.00 |
| $10^{-5}$ | 0 | 77 | 0.00 |

TABLE 4-continued

| Dilution of positive control leaf extract | Phage A and Phage K mix used | Phage K only used | Potato Virus × ELISA (OD450) |
|---|---|---|---|
| $10^{-1}$ dilution of negative control leaf extract | 0 | 83 | 0.00 |

Conclusion

This experiment demonstrates the advantage of using the two phage approach compared to a single phage approach. When Phage K alone was used there was a significant number of colonies in the negative control. The two phage approach reduces the background signal so that the positive samples are readily identified, even at a dilution of $10^{-3}$. The background signal can be further reduced by the use of a surfactant, for example that sold under the trade mark Tween 20 in a concentration of from 0.1 to 0.5% v/v and/or bovine serum albumen at concentrations of up to 5% w/v in the incubation or washing media.

The PathoScreen ELISA as supplied by the manufacturers was not as sensitive as the method of the invention.

EXAMPLE 4

An Alternative Two Phage Strategy for Detection of Virus

Anti-potato x virus conjugated Phage A or Phage K (prepared as in Example 3) were used to coat microtiter plate wells (Greiner Labortechnik Ltd., Cambridge, UK, 756061). Dilutions of plant extract were captured in phage-coated wells. After washing, phage/antibody conjugate (Phage A or Phage K) were added to each well such that Phage A was added to the wells which had been coated with Phage K and vice versa. After incubation to allow capture of the phage, the wells were washed and log phase TG1 added to achieve infection. After infection, the contents of each well were plated out on solid media containing ampicillin and kanamycin to select for dually infected cells. After selection the numbers of colonies on each plate were counted and the results are set out in Table 5:

TABLE 5

| Dilution of positive control leaf extract | Capture with Phage A | Capture with Phage K |
|---|---|---|
| $10^{-1}$ | ++ | ++ |
| $10^{-2}$ | ++ | 484 |
| $10^{-3}$ | 442 | 43 |
| $10^{-4}$ | 56 | 0 |
| $10^{-5}$ | 0 | 0 |
| $10^{-1}$ dilution of negative control leaf extract | 0 | 0 |

Conclusion

This test demonstrates that binding of the virus to the target material in two stages offers a successful alternative to binding of the phage particles in a single stage and enables $10^{-4}$ dilution of positive control leaf extract to be detected.

What is claimed is:

1. A method for detecting a target material in a sample, which method comprises the steps of:

a. Exposing a sample, expected to contain that target material or in which that target material is to be localised, to two or more viruses which are capable of binding directly or indirectly with that target material so as to form a virally bound target material and conjointly to endow the virally bound target material with a distinctive property which -s not conferred on the target material by either virus alone; and b. Cultivating the product from stage a in the presence of an indicator material to which the viruses carried by the virally bound target material attach so as to cause the indicator material to adopt the distinctive property of the virally bound target material; and c. Monitoring the presence or otherwise of virally attached indicator material.

2. A method as claimed in claim 1, characterised in that the cultivation stage b is carried out under conditions which the virally attached indicator material survives but which indicator material to which none or only one of the viruses have attached does not survive.

3. A method as claimed in claim 1, characterised in that the virus moiety is bound to the target material through an intermediate ligand.

4. A method as claimed in claim 1, characterized in that the viral moieties endow the virally bound target material with resistance to two different forms of anti-biotic.

5. A method as claimed in claim 1, characterized in that stage b is carried out in the presence of an indicator bacterial culture.

6. A method as claimed in claim 5, characterised in that the cultivation in stage b is carried out in the presence of at least the statistically required amount of bacterial cells.

7. A method according to claim 1, characterised in that a virus is used which endows the virally infected indicator material with a visually detectable feature.

8. A method as claimed in claim 1, characterised in that the target material is an inorganic or organic chemical or an organism, a part thereof or a expression or product of an organism.

9. A method as claimed in claim 8, characterised in that the target material is a protein, enzyme, prion, lipid, nucleic acid, hormone, fungi, virus, bacterium or protozoa.

10. A method as claimed in claim 1, characterized in that the target material is the result of an interaction between two or more other materials and the method is used to determine the extent or inhibition of such an interaction.

11. A method as claimed in claim 10, characterised in that the interaction is inhibited by the action of a third component and the effect of that third component is assessed by the extent of inhibition of the production of the interaction product.

12. A method as claimed in claim 1, characterised in that the target material is a contaminant or impurity in another material and the method is used to detect the presence of that contaminant or impurity.

13. A method as claimed in claim 1, characterised in that the target material is a medicament or biocide or the result of the interaction of a medicament or biocide with an organism and the method is used to detect the efficacy of the medicament or biocide.

14. A method as claimed in claim 1, characterized in that the detection of the distinctive property in the indicator material is monitored over a period of time so as to give a quantitative indication of the target material present in the sample.

15. A kit of ingredients for use in the method of claim 1, characterised in that it comprises:

a. At least two phage materials which are adapted to bind to a common target material or to components which interact to form the target material and which endow that target material with a distinctive property; and b. an indicator material suitable for cultivation in a growth medium and adapted to adopt the distinctive property endowed by the phage materials.

16. A kit as claimed in claim 15, characterized in that the indicator material is a bacterium which can be infected by the phage materials.

17. A kit as claimed in claim 15, characterised in that the phage materials and the bacterium are in freeze dried solid particulate form.

18. A kit as claimed in claim 15, characterized in that it also comprises a growth medium for the cultivation of the virally bound target material and the indicator material.

19. A kit as claimed in claim 15, characterized in that it comprises an additional ingredient which provides visually detectable indication of the growth of indicator material infected by the phage materials.

20. A method for detecting a target material in a sample which method comprises the acts of:

a. linking at least two viruses together through the target material so as to form a virally bound target material and conjointly to endow the virally bound target material with a distinctive property which is not conferred on the target material by either virus alone;

b. Cultivating the product from stage a in the presence of an indicator material to which the viruses carried by the virally bound target material attach so as to cause the indicator material to indicate the distinctive property of the virally bound target material; and c. Monitoring the presence or otherwise of virally attached indicator material.

21. A method as claimed in claim 20, wherein the viruses are bound to the target material through a ligand.

22. A method as claimed in claim 20, wherein the viruses each cause the virally attached indicator material to display a respective distinctive property.

23. A method as claimed in claim 22, wherein the viruses endow the virally bound target material with the ability to confer on a suitable bacterial indicator material resistance to a respective antibiotic.

* * * * *